United States Patent [19]

Camenzind

[11] Patent Number: 5,433,873
[45] Date of Patent: Jul. 18, 1995

[54] PHOSPHORUS-FREE LUBRICANT ADDITIVES

[75] Inventor: Hugo Camenzind, Bern, Switzerland

[73] Assignee: Ciba-Geigy Corporation, Ardsley, N.Y.

[21] Appl. No.: 140,574

[22] Filed: Oct. 21, 1993

[30] Foreign Application Priority Data

Oct. 30, 1992 [CH] Switzerland ............... 3389/92

[51] Int. Cl.$^6$ ............... C10M 135/36; C07D 251/38; C07D 251/00
[52] U.S. Cl. ............... 252/47; 252/47.5; 252/78.1; 544/180; 544/194; 544/212; 544/215
[58] Field of Search ............... 544/180, 194, 212, 215; 252/47

[56] References Cited

U.S. PATENT DOCUMENTS

| | | | |
|---|---|---|---|
| 3,154,490 | 10/1964 | Rai et al. | 252/47 |
| 3,156,690 | 11/1964 | Dexter et al. | 252/47 |
| 3,175,974 | 3/1965 | Rai et al. | 252/47 |
| 3,705,155 | 12/1972 | Miller | 544/215 |
| 3,966,623 | 6/1976 | Krug et al. | 252/47 |
| 4,737,302 | 4/1988 | Camenzind et al. | 252/47 |
| 4,764,298 | 8/1988 | Croudace | 252/47 |
| 4,794,134 | 12/1988 | Wheeler et al. | 524/100 |
| 4,894,091 | 1/1990 | Braig et al. | 252/391 |
| 4,972,010 | 11/1990 | Wheeler et al. | 524/100 |
| 5,118,431 | 6/1992 | Nader | 252/47 |
| 5,171,855 | 12/1992 | Borzatta et al. | 544/212 |
| 5,212,307 | 5/1993 | Wilczak | 544/194 |

FOREIGN PATENT DOCUMENTS

| | | |
|---|---|---|
| 0174262 | 9/1985 | European Pat. Off. . |
| 0203033 | 11/1986 | European Pat. Off. . |
| 0259254 | 3/1988 | European Pat. Off. . |
| 0365127 | 4/1990 | European Pat. Off. . |
| 2384282 | 10/1978 | France . |
| 0154572 | 4/1982 | Germany . |

OTHER PUBLICATIONS

J. Chem. Soc. (C), 1967, 466 (month unknown).
Derwent Abst. WPI Acc No:82-72431E/35.
Derwent Abst. WPI Acc No:78-76453A/43.
Indian Journal of Pharmaceutical Sciences (May 1992).

Primary Examiner—Ellen M. McAvoy
Attorney, Agent, or Firm—Michele A. Kovaleski

[57] ABSTRACT

The invention relates to novel compounds of formula I

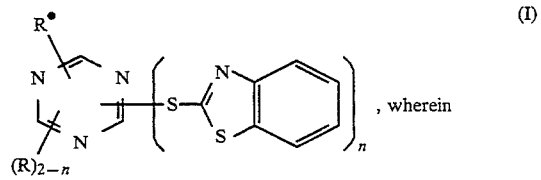

, wherein n is 1 or 2,

R and R* are each independently of the other $-OR_1$, $-SR_2$ or $-NR_3R_4$, $R_1$ is hydrogen, $C_1$-$C_{30}$alkyl, $C_5$-$C_7$cycloalkyl, phenyl or naphthyl, phenyl- or naphthyl-substituted $C_1$-$C_{18}$alkyl or phenyl or naphthyl which are substituted by $C_1$-$C_{12}$alkyl, $C_1$-$C_{12}$alkoxy or $C_1$-$C_{12}$hydroxyalkyl, $R_2$ is $C_1$-$C_{30}$alkyl, phenyl or naphthyl, phenyl- or naphthyl-substituted $C_1$-$C_{18}$alkyl or phenyl or naphthyl which are substituted by $C_1$-$C_{12}$alkyl, $C_1$-$C_{12}$alkoxy or $C_1$-$C_{12}$hydroxyalkyl, or is a radical of formula $(CH_2)_p-CO-OR_5$, p is 1 or 2, $R_3$ and $R_4$ have each independently of the other the meanings of $R_1$, or $-NR_3R_4$ is piperidyl, pyrrolidyl or azepyl, and $R_5$ is hydrogen, $C_1$-$C_{30}$alkyl, $C_5$-$C_7$cycloalkyl, phenyl or naphthyl, phenyl- or naphthyl-substituted $C_1$-$C_{18}$alkyl or phenyl or naphthyl which are substituted by $C_1$-$C_{12}$alkyl, $C_1$-$C_{12}$alkoxy or $C_1$-$C_{12}$hydroxyalkyl.

The compounds may be used as lubricant additives.

12 Claims, No Drawings

PHOSPHORUS-FREE LUBRICANT ADDITIVES

The present invention relates to novel heterocyclic compounds and to the use thereof as additives in lubricant compositions.

It is common practice to add a number of chemicals to lubricants, on the one hand to prolong the life of the lubricant itself and, on the other, to protect the metal pans to be lubricated from wear and tear. Owing to the increasingly exacting demands made of modern lubricants and to longer changing intervals there is a constant search for new effective additives. The emphasis is increasingly being placed on metal- and phosphorus-free compounds, as these have useful properties if combustion engines fitted with catalytic converters are to be lubricated.

The preparation of 2,4,6-tris(benzothiazol-2-ylthio)-1,3,5-triazine is described by W. F. Beech in J. Chem. Soc. (C), 1967, 466. Lubricant additives of formula

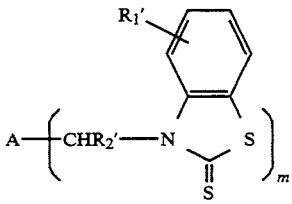

wherein m is 1 or 2 and A is —NR'R''', >NR' or —NR'—R'''—NR'—, and the nature of the substituents R'$_1$, R'$_2$, R', R'' and R''' is here not important, are disclosed in U.S. Pat. No. 4,737,302.

EP-A-0 365 127 discloses substituted triazines of formula

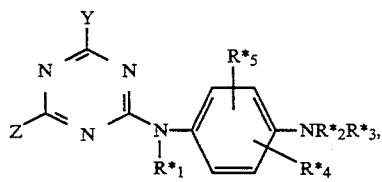

wherein Z and Y, in addition to many other meanings, may be

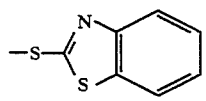

and the meaning of the substituents R*$_1$, R*$_2$, R*$_3$, R*$_4$ and R*$_5$ are not of interest in this context. The compounds are very effective antiozonants for rubber.

It has now been found that the metal- and phosphorus-free compounds described hereinbelow are surprisingly good extreme-pressure and antiwear additives for lubricants as well as being effective antioxidants.

Accordingly, the invention relates to compounds of formula I

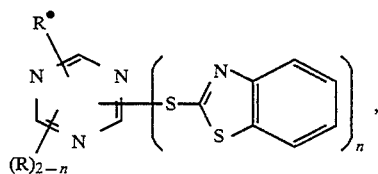

wherein
n is 1 or 2,
R and R• are each independently of the other —OR$_1$, —SR$_2$ or —NR$_3$R$_4$,
R$_1$ is hydrogen, C$_1$–C$_{30}$alkyl, C$_5$–C$_7$cycloalkyl, phenyl or naphthyl, phenyl- or naphthyl-substituted C$_1$–C$_{18}$alkyl or phenyl or naphthyl which are substituted by C$_1$–C$_{12}$alkyl, C$_1$–C$_{12}$alkoxy or C$_1$–C$_{12}$hydroxyalkyl,
R$_2$ is C$_1$–C$_{30}$alkyl, phenyl or naphthyl, phenyl- or naphthyl-substituted C$_1$–C$_{18}$alkyl or phenyl or naphthyl which are substituted by C$_1$–C$_{12}$alkyl, C$_1$–C$_{12}$alkoxy or C$_1$–C$_{12}$hydroxyalkyl, or is a radical of formula (CH$_2$)$_p$—CO—OR$_5$,
p is 1 or 2,
R$_3$ and R$_4$ have each independently of the other the meanings of R$_1$, or —NR$_3$R$_4$ is piperidyl, pyrrolidyl or azepyl, and
R$_5$ is hydrogen, C$_1$–C$_{30}$alkyl, C$_5$–C$_7$cycloalkyl, phenyl or naphthyl, phenyl- or naphthyl-substituted C$_1$–C$_{18}$alkyl or phenyl or naphthyl which are substituted by C$_1$–C$_{12}$alkyl, C$_1$–C$_{12}$alkoxy or C$_1$–C$_{12}$hydroxyalkyl.

Preferred compounds of formula I are those wherein
R$_1$ is C$_1$–C$_{18}$alkyl,
R$_2$ is C$_1$–C$_{18}$alkyl or CH$_2$—CO—OR$_5$,
R$_3$ and R$_4$ are each independently of the other hydrogen, C$_1$–C$_{18}$alkyl or benzyl, or —NR$_3$R$_4$ is piperidyl, pyrrolidyl or azepyl, and
R$_5$ is C$_1$–C$_{18}$alkyl.

Particularly preferred compounds of formula I are those wherein
R and R• are each independently of the other —SR$_2$ or —NR$_3$R$_4$,
R$_2$ is C$_4$–C$_{12}$alkyl,
R$_3$ and R$_4$ are each independently of the other C$_1$–C$_{12}$alkyl, and
R$_5$ is C$_1$–C$_{18}$alkyl.

Very particularly preferred compounds are those wherein n=2, R$_2$ is octyl or CH$_2$—CO—O—R$_5$, and R$_1$, R$_3$, R$_4$ and R$_5$ are n-octyl, 2-ethylhexyl or isooctyl, and also compounds wherein n=1, R and R• are —SR$_2$ and R$_2$ is CH$_2$—CO—O—isooctyl or CH$_2$—CO—OR$_5$.

If n is 1, R and R• are preferably identical.

Alkyl substituents in the compounds of formula I may contain from 1 to 30, preferably from 1 to 18, carbon atoms. Typical examples of such substituents are methyl, ethyl, propyl, butyl, pentyl, hexyl, octyl, nonyl, decyl, undecyl, dodecyl, tetradecyl, hexadecyl, octadecyl, eicosyl or docosyl as well as corresponding branched isomers, preferably tert-butyl, isooctyl (2-ethylhexyl) and its mixtures of isomers, as well as isododecyl. Alkoxy radicals are derived in obvious manner from these groups, as are also alkylene radicals which are contained in the definitions of the substituents shown in formula I.

Phenyl- or naphthyl-substituted alkyl is preferably benzyl, phenethyl, 3-phenylpropyl, α-methylbenzyl and α,α-dimethylbenzyl. Benzyl is preferred.

$C_5$–$C_7$Cycloalkyl is cyclopentyl, cyclohexyl or cycloheptyl.

Phenyl or naphthyl which are substituted by $C_1$–$C_{12}$alkyl, $C_1$–$C_{12}$alkoxy or $C_1$–$C_{12}$hydroxyalkyl may typically be tolyl, xylyl, cumyl, hydroxybenzyl, 3,5-di-tert-butylhydroxybenzyl or methoxybenzyl. It is preferred that the aromatic ring system contains 1 or 2 substituents.

The invention further relates to compositions comprising
A) a lubricant, a hydraulic fluid or a machining fluid, and
B) at least one compound of formula I.

Component A) is preferably a lubricant.

The lubricants, hydraulic fluids and machining fluids contained in the novel compositions may decompose more or less readily when exposed to heat, light or radiation, to mechanical load (especially though shear forces) and to chemical reagents (especially atmospheric oxygen).

The compounds of formula I afford protection against such influences and will conveniently be present in the novel compositions in amounts of 0.01 to 10% by weight, typically 0.05 to 5% by weight, preferably 0.05 to 3% by weight and, most preferably, 0.1 to 2% by weight. The novel compositions may contain one or more than one of these compounds, and the percentages by weight are based on the total amount of said compounds. The basis of calculation is the total weight of the lubricant, machining fluid or hydraulic fluid without the compounds of formula I.

The invention thus also relates to the use of compounds of formula I as additives for lubricants, hydraulic fluids and machining fluids, especially as, antioxidants, extreme-pressure and antiwear additives. The inventive utility also embraces the protection of the metal pans to be lubricated from mechanical wear (wear protection). Such a utility also entails a process for enhancing the performance properties of lubricants, hydraulic fluids and machining fluids. It will be readily understood that a novel lubricant composition can be used as motor oil.

The suitable lubricants, hydraulic fluids and machining fluids are typically based on mineral or synthetic oils or mixtures thereof. The lubricants are known to the skilled person and are described in the relevant literature, inter alia in Dieter Klamann, "Schmierstoffe und verwandte Produkte" (Lubricants and Related Products) (Verlag Chemic, Weinheim, 1982), in Schewe-Kobek, "Das Schmiermittel-Taschenbuch" (Handbook of Lubricants) (Dr. Alfred Hüthig-Verlag, Heidelberg, 1974), and in "Ullmanns Enzyklopädie der technischen Chemic" (Ullmann's Encyclopedia of Industrial Chemistry), Vol. 13, pages 85–94 (Verlag Chemic, Weinheim, 1977).

The lubricants are preferably oils and fats and are typically derived from a mineral oil. Oils are preferred.

A further group of lubricants suitable for use in the practice of this invention comprises vegetable or animal oils, fats, tallows and waxes or mixtures with one another or with the mineral or synthetic oils referred to above. Vegetable and animal oils, fats, tallows and waxes are typically palm nut oil, palm oil, olive oil, beet oil, rapeseed oil, linseed oil, ground nut oil, soybean oil, cottonseed oil, sunflower seed oil, pumpkin seed oil, coconut oil, corn oil, castor oil, walnut oil and mixtures thereof, fish oils, the tallows of slaughter animals, e.g. beef tallow, neat's foot and bone oil, as well as the modified, epoxidised and sulfoxidised forms thereof, typically epoxidised soybean oil.

The mineral oils me based in particular on hydrocarbon compounds.

Synthetic lubricants typically comprise lubricants based on aliphatic or aromatic carboxylates, polymeric esters, polyalkylene oxides, phosphates, poly-α-olefins or silicones, on a diester of a divalent acid with a monohydric alcohol, typically dioctyl sebacate or dinonyl adipate, on a triester of trimethylolpropane with a monovalent acid or with a mixture of acids, conveniently trimethylolpropane tripelargonate, trimethylolpropane tricaprylate or mixtures thereof, on a tetraester of pentaerythritol with a monovalent acid or with a mixture of such acids, typically pentaerythritol tetracaprylate, or on a complex ester of monovalent and divalent acids with polyhydric alcohols, for example a complex ester of trimethylolpropane with caprylic and sebacic acid or of a mixture thereof. Especially suitable lubricants are, in addition to mineral oils, typically poly-α-olefins, ester-based lubricants, phosphates, glycols, polyglycols and polyalkylene glycols and mixtures thereof with water.

Machining fluids and hydraulic fluids can be prepared from the same substances as those described above in connection with the lubricants. Often they are also emulsions of such substances in water or other liquids.

The lubricating compositions of this invention are used, inter alia, for combustion engines, typically for motor vehicles.

The compounds of formula I are readily soluble in lubricants, machining fluids and hydraulic fluids and are therefore especially suitable for use as additives for lubricants, machining fluids and hydraulic fluids. Their surprisingly good antioxidative and antiwear properties merit special mention.

The invention therefore also relates to a process for enhancing the performance properties of lubricants, machining fluids and hydraulic fluids, which comprises adding thereto compounds of formula I.

The lubricants, machining fluids and hydraulic fluids of this invention may also contain other additives which are added for further enhancement of the basic properties. These further additives comprise antioxidants, metal deactivators, rust inhibitors, viscosity improvers, pour-point depressants, dispersants, detergents, other extreme-pressure and antiwear additives.

Illustrative examples of such further additives are:

Examples of phenolic antioxidants

1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethy lphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylunde c-1'-yl)phenol, 2,4-dimethyl-6-(1'-methylheptadec-1'-yl)phenol, 2,4-dimethyl-6-(1'-methyltridec-1'-yl)phenol and mixtures thereof.

2. Alkylthiomethylphenols, for example 2,4-dioctylthiomethyl-6-tert-butylphenol, 2,4-dioctylthiomethyl-6-methy lphenol, 2,4-dioctylthiomethyl-6-ethylphenol and 2,6-didodecylthiomethyl-4-nonylphenol.

3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate and bis-(3,5-di-tert-butyl-4-hydroxyphenyl) adipate.

4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol) and 4,4'-bis-(2,6-dimethyl-4-hydroxyphenyl) disulfide.

5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl) phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert- butyl-4-isobutylphenol), 2,2'-methylenebis[6-(α-methylbenzyl)-4-nonyl phenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxyb enzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis-(3'-tert-butyl-4'-hydroxyphenyl)butyrate], bis(3-tert-butyl-4-hydroxy-5 -methylphenyl)dicyclopentadiene, bis[2-(3'-tert-butyl-2'hydroxy-5'-methylbenzyl )-6-tert-butyl-4 -methylphenyl]terephthalate, 1,1-bis(3,5-dimethyl-2-hydroxyphenyl)butane, 2,2-bis(3,5-di-tert-butyl-4hydroxyphenyl)propane, 2,2-bis(5-tert-butyl-4-hydroxy-2-methylphenyl)-4 -n-dodecylmercaptobutane and 1,1,5,5-tetra(5-tert-butyl-4-hydroxy-2-methylphenyl)pentane.

6. O—, N— and S-Benzyl compounds, for example 3,5,3',5'-tetra-tert-butyl-4,4'-dihydroxydibenzyl ether, octadecyl 4-hydroxy-3,5-dimethylbenzyl-mercaptoacetate, tris(3,5-di-tert-butyl-4-hydroxybenzyl)amine, bis(4-tert-butyl-3-hydroxy-2,6-dimethylbenzyl)-dithioterephthalate, bis(3,5-di-tert-butyl-4-hydroxybenzyl) sulfide and isooctyl 3,5-di-tert-butyl-4-hydroxybenzyl-mercaptoacetate.

7. Hydroxybenzylated malonates, for example dioctadecyl 2,2-bis(3,5-di-tert-butyl-2hydroxybenzyl)malonate, dioctadecyl 2(3-tert-butyl-4-hydroxy-5-methylbenzyl)malonate, didodecylmercaptoethyl 2,2-bis(3,5-di-tert-butyl-4-hydroxybenzyl)malonate and bis[4-(1,1,3,3-tetramethylbutyl)phenyl] 2,2-bis(3,5-di-tert-butyl-4-hydroxybenzyl)malonate.

8. Aromatic hydroxybenzyl compounds, for example 1,3,5-tris(3,5-di-tert-butyl-4-hydroxybenzyl)-2,4,6-trimethyl benzene, 1,4-bis(3,5-di-tert-butyl-4-hydroxybenzyl)-2,3,5,6-tetramethylbenzene and 2,4,6-tris(3,5-di-tert-butyl-4-hydroxybenzyl)phenol.

9. Triazine compounds, for example 2,4-bis(octylmercapto)-6-(3,5-di-tert-butyl-4-hydroxyanilino)- 1,3,5-triazine 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxy benzyl)isocyanurate, 1,3,5-tris(4-tert-butyl-3-hydroxy-2,6-dimethylbenzyl) isocyanurate, 2,4,6-bis(3,5-di-tert-butyl-4-hydroxyphenylethyl)- 1,3,5-triazine, 1,3,5-tris(3,5-di-tert-butyl-4-hyd roxyphenylpropionyl)hexahydro-1,3,5-triazine and 1,3,5-tris(3,5-di-cyclohexyl-4-hydroxybenzyl) isocyanurate.

10. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate and the calcium salt of monoethyl 3,5-di-tert-butyl-4-hydroxybenzylphosphonate.

11. Acylaminophenols, for example 4-hydroxylauranilide, 4-hydroxystearanilide and octyl N-(3,5-di-tert-butyl-4-hydroxyphenyl)carbamate.

12. Esters of β-(3,5-di-tert-butyl-4-hydroxyphenyl)-propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

13. Esters of β-(5-tert-butyl-4-hydroxy-3-methylphenyl)propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

14. Esters of β-(3,5-dicyclohexyl-4-hydroxyphenyl)-propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, diethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane and 4-hydroxymethyl-1-phospha-2,6,7-trioxabicyclo-[2.2.2]-octane.

15. Esters of 3,5-di-tert-butyl-4-hydroxyphenylacetic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxmmide, 3-thiaundecanol, 3-thiapentadecanol, trimethylhexanediol, trimethylolpropane and 4-hydroxymethyl-1-phospha-2,6,7-trioxabicyclo[2.2.2]octane.

16. Amides of β-(3,5-di-tert-butyl-4-hydroxyphenyl)-propionic acid, for example N,N'-bis(3,5-di-tert-butyl-4 -hydroxyphenylpropionyl)hexamethylenediamine, N,N'-bis(3,5-di-tert-butyl-4-hydroxyphenylpropionyl)-trimethylenediamine and N,N'-bis(3,5-di-tert-butyl-4-hydroxyphenylpropionyl)hydrazine.

Examples of aminic antioxidants:

N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)- p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis(-phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetra-phenyl-1,4-diaminobut-2-ene, N,N-bis(2,2,6,6-tetramethylpiperid-4-yl-hexamethylenediamine, bis(2,2,6,6-tetramethylpiperid- 4-yl) sebacate, 2,2,6,6-tetramethylpiperidin-4-one and 2,2,6,6-tetramethylpiperidin-4-ol.

Examples of other antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, for example for copper, are:

a) Benzotriazoles and derivatives thereof, for example 4- or 5-alkylbenzotriazoles (e.g. tolutriazole) and derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl)tolutriazole and 1-[bis(2-ethylhexyl)aminomethyl)benzotriazole; and alkoxyalkylbenzotriazoles such as 1-(nonyloxymethyl)benzotriazole, 1-(1-butoxyethyl)benzotriazole and 1-(1-cyclohexyloxybutyl)tolutriazole.

b) 1,2,4-Triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles.

c) Imidazole derivatives, for example 4,4'-methylenebis(2-undecyl-5-methylimidazole) and bis[(N-methyl)imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thia diazolin-2-one.

e) Amino compounds, for example salicylidenepropylenediamine, salicylaminoguanidine and salts thereof.

Examples of rust inhibitors are:

a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(carboxyethyl)-1-dodecyl-3-methylglycerol and the amine salts thereof.

b) Nitrogen-containing compounds, for example:
I. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.
II. Heterocyclic compounds, for example: substituted imidazolines and oxazolines, and 2-heptadecenyl-1-(2-hydroxyethyl)imidazoline.

c) Phosphorus-containing compounds, for example: Amine salts of phosphoric acid partial esters; or phosphonic acid partial esters, and zinc dialkyldithiophosphates.

d) Sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and salts thereof.

e) Glycerol derivatives, for example: glycerol monooleate, 1-(alkylphenoxy)-3-(2-hydroxyethyl)-glycerols, 1-(alkylphenoxy)-3-(2,3-dihydroxypropyl)glycerols and 2-carboxyalkyl-1,3-dialkyl glycerols.

Examples of viscosity index improvers are:

Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are:

Polymethacrylate and alkylated naphthalene derivatives.

Examples of dispersants/surfactants are:

Polybutenylsuccinic amides or -imides, polybutenylphosphonic acid derivatives and basic magnesium, calcium and barium sulfonates and phenolates.

Examples of antiwear additives are:

Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-

[(diisopropoxyphosphinothioyl)thio]propionate, triphenyl thiophosphate (triphenylphosphorothioate), tris-(alkylphenyl) phosphorothioate and mixtures thereof (for example u-is(isononylphenyl) phosphorothioate), diphenyl monononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris[isooctyl 2-acetate], derivatives of 2-mercaptobenzothiazole such as 1-[N,N-bis(-2-ethylhexyl)aminomethyl]-2-mercapto-1H-1,3-benzothiazole, and ethoxycarbonyl-5-octyldithiocarbamate.

The compounds of formula I are novel.

The reaction of cyanuric chloride with different protic reactants containing >N—H, —OH or —SH groups is known (W. F. Beech, J. Chem. Soc. C, 1967 466–72). As these substituents normally exert an deactivating effect on the further reactive positions of the cyanuric chloride, it is possible to replace the chlorine atoms stepwise. Different solvents such as acetone, benzene or also water may conveniently be used, in some cases also two-phase mixtures. Acetone and acetone/water mixtures have been found useful.

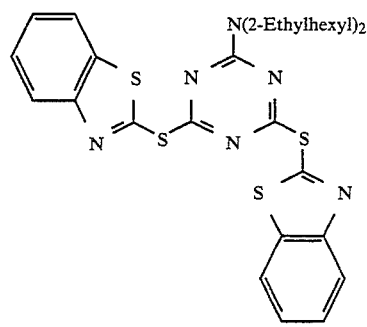

245 mi of bis(2-ethylhexyl)amine are added dropwise over 10 min at 0°–5° C. to a solution of 147.5 g of cyanuric chloride in 2 1 of acetone. Over a further 10 min, 400 ml of 2N aqueous sodium hydroxide are added dropwise at 0°–5° C. The reaction mixture is stirred for 20 min at 0°–5° C., then poured into 2 1 of water and extracted with 1 1 of hexane. The extract is concentrated by evaporation, giving 304 g of 2,4-dichloro-6-(N,N-

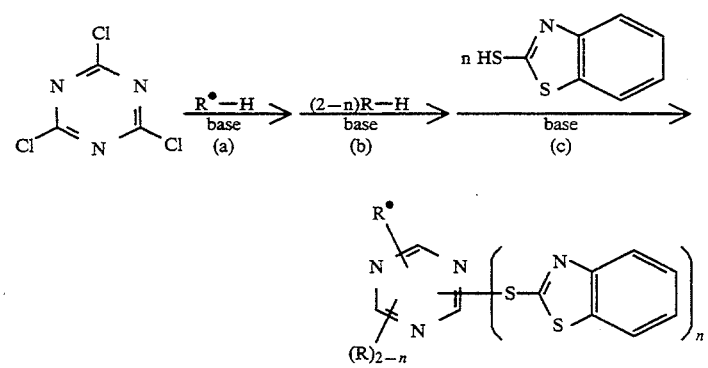

The compounds of formula I in which R and R• are identical [(a) and (b) together form one step in the above scheme] or n is 2 [(b) is omitted] are therefore prepared in a two-step synthesis starting from cyanuric chloride. The cyanuric chloride is dissolved with 1 or 2 molar equivalents of amine, mercaptan or alcohol in a suitable solvent, conveniently acetone, and treated at 0°–5° C. with 1 or 2 molar equivalents of a base (e.g. tertiary amine, KOH or NaOH). The mono- or dichloro intermediate can then be further reacted in solution with 2 or with 1 molar equivalent of 2-mercaptobenzothiazole and 1 or 2 molar equivalents of a base at room temperature to 60° C., the base being conveniently used in a slight excess. When R and R• are different, then one more step is necessary [steps (a), (b) and (c) in the scheme]. When R or R• is NR₃R₄, it is best to effect reaction first with 1 equivalent of amine, as it deactivates more strongly than OH— or SH compounds.

The starting —SH, —OH and >NH compounds are known per se or can be prepared by per se known methods or are commercially available.

The following Examples illustrate the invention in more detail. Unless otherwise indicated, all parts and percentages are by weight. Isooctyl denotes the alkyl groups of a mixture of isomers obtainable as 2-mercaptoisooctylacetate.

Example 1: 2,4-Bis(2-mercaptobenzothiazol-S-yl)-6-(N,N-di-2-ethylhexylamino)-1,3,5-triazine bis[2-ethylhexylamino])-1,3,5-tri azine as a pale yellow oil.

To a solution of 4.1 g of the above compound in 30 ml of ethanol/water 3:1 are added 4.2 g of 2-mercaptobenzothiazole, followed by the addition of a solution of 1 g of NaOH in 10 ml of water. The reaction mixture is stirred for 15 h at reflux, then diluted with water in a separating funnel and extracted with hexane. The hexane phase is washed with a small amount of 2N aqueous sodium hydroxide, brine and water, and concentrated by evaporation. The crude product is purified over a short column of 120 g of silica gel (gradient elution with hexan/toluene/2% ethanol). The solvent is removed, giving 4.1 g of a clear, pale yellow viscous oil (63% of theory).

| Microanalysis: | C | H | N | S |
|---|---|---|---|---|
| calcd | 60.89% | 6.50% | 12.91% | 19.74% |
| found | 61.65% | 6.92% | 12.34% | 18.76% |

Example 2: 2,4-Bis(2-mercaptobenzothiazol-S-yl)-6-(n-octylthio)-1,3,5-triazine

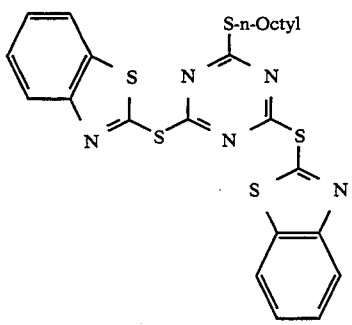

To a solution of 188.2 g of cyanuric chloride in 1.5 l of acetone are added 151 g of n-octanethiol, followed by the addition of 510 ml of 2N aqueous sodium hydroxide at 0°–5° C. over 30 min. The emulsion is stirred for 1 h at 0°–5° C. and for a further hour at 5°–15° C., poured into water and extracted with 500 ml of toluene. The extract is washed with brine and water and the solvent is stripped off, giving 265 g of 2,4-dichloro-6-(n-octanethiol-S-yl)-1,3,5-triazin e as a clear, pale yellow oil (90% of theory).

124 g of this oil are dissolved in 1 l of acetone. Then 155 g of 2-mercaptobenzothiazole and 480 ml of 2N aqueous sodium hydroxide are added in succession at 22°–32° C. over 30 min. The reaction mixture is stirred for 1 h at room temperature and poured into 1 l of brine and extracted with 500 ml of toluene. The organic phase is washed with brine and water and the solvent is removed. The crude product (210 g) is dissolved in 200 ml of toluene and the solution is slowly mixed, with stirring, with 3×300 ml of hexane. The product crystallises over 30 min. After a further 30 minutes the crystalline product is filtered with suction and washed with a small amount of hexane. Yield: 185 g of pale yellowish crystals (83% of theory), m.p. 75°–77° C.

| Microanalysis: | C | H | N | S |
|---|---|---|---|---|
| calcd | 54.02% | 4.53% | 12.60% | 28.84% |
| found | 54.85% | 4.53% | 12.21% | 28.09% |

Example 3: 2,4-Bis(2-mercaptobenzothiazol-S-yl)-6-(2-mercaptoisooctylacetate-S-yl)-1,3,5-triazine

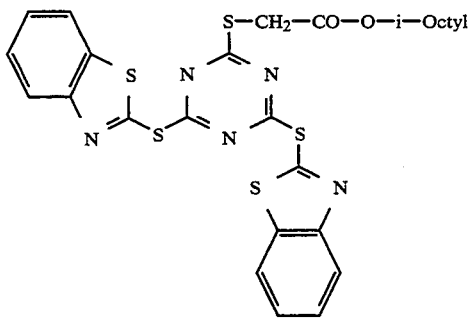

To a solution of 92.2 g of cyanuric chloride in 1 l of acetone are added 102.1 g of 2-mercaptoisooctylacetate (mixture of isomers), followed by the addition of 61.8 g of collidine at −20° C. over 20 min. The mixture is heated over 30 min to 0°–5° C., poured on to 1.5 l of ice-water and extracted with 1 l of hexane. The solvent is removed by evaporation and the crude product is purified over a short column of 400 g silica gel (gradient elution with hexane/toluene). The solvent is stripped off, giving 142 g of 2,4-dichloro-6-(2-mercaptoisooctylacetate-S-yl)-1 ,3,5-triazine as a slightly orange coloured oil (81% of theory).

To a solution of 17.6 g of this oil in 400 ml of acetone are added 18.4 g of 2-mercaptobenzothiazole, followed by the dropwise addition of 16.7 ml of triethylamine at room temperature to 30° C. over 15 min. The reaction mixture is stirred for 1 h at room temperature and poured into 500 ml of ice-water and extracted with 500 ml of hexane and 500 ml of toluene. The organic phase is washed with a small mount of 2N aqueous sodium hydroxide, brine and water and concentrated by evaporation. The crude product is purified over a short column of 200 g of silica gel (gradient elution with toluene/1% ethyl acetate) and concentrated, giving 19.7 g (64% of theory) of a pale orange crystalline solid of m.p. 75°–78° C.

| Microanalysis: | C | H | N |
|---|---|---|---|
| calcd | 52.83% | 4.43% | 11.41% |
| found | 52.79% | 4.55% | 11.46% |

Example 4: 2-(2-Mercaptobenzothiazol-S-yl)-4,6-bis(2-mercaptoisooctylacetate-S-yl)-1,3,5-triazine

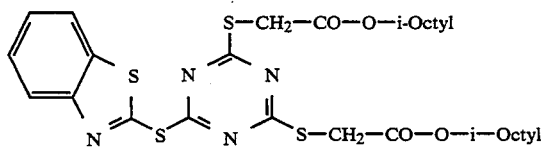

To a solution of 92.2 g of cyanuric chloride in 1 l of acetone are added 102.1 g of 2-mercaptoisooctylacetate (mixture of isomers), followed by the addition of 61.8 g of collidine at −20° C. over 20 min. The mixture is warmed to 0°–5° C. over 30 min. Again 102.1 g of 2-mercaptoisooctylacetate (mixture of isomers) are added, followed by the addition of 61.8 g of collidine at −20° C. over 20 min. The orange suspension is further stirred for 10 h at room temperature, poured into 1 l of water and extracted with 500 ml of toluene. The solvent is removed by evaporation and the crude product is purified over a short column of 400 g of silica gel (gradient elution with hexane/toluene). The solvent is removed, giving 245 g of 2-chloro-4,6-bis(2-mercaptoisooctylacetate-S-yl)-1,3,5-triazine as a pale, medium viscosity oil (94% of of theory).

To a solution of 26 g of this compound in 300 ml of toluene are added 9.2 g of mercaptobenzothiazole and then 9 ml of triethylamine. The clear brown solution is heated to 60° C. and stirred for 30 min at this temperature. The suspension is washed in succession with water, a minor amount of 2N aqueous sodium hydroxide, brine and water and concentrated by evaporation. The crude product is purified over a short column of 400 g of silica gel (gradient elution with hexane/toluene/2% ethyl acetate). The eluant is removed, giving 21.5 g of a clear, pale yellow viscous oil (66% of theory).

| Microanalysis: | C | H | N | S |
| --- | --- | --- | --- | --- |
| calcd | 60.89% | 12.51% | 19.74% | 19.74% |
| found | 61.65% | 6.92% | 12.34% | 18.76% |

Example 5: Test for antiwear protection

The antiwear test is carded out by ASTM standard method D-2783-81 using the Shell 4-ball apparatus. The base oil used in the test is STOCK 305 available from Mobil, to which the amount of compound indicated in Table II is added in accordance with each Example. The values determined are:
   a) the weld load (WL) as the load (in kg) at which welding of the 4 balls occurs over 10 s, and
   b) the average WSD (wear scar diameter) at a load of 20 kg over 1 hour at 60° C. (in mm).

The results are reported in Table I.

TABLE I

| Compound of Example | Amount added [%] | WL [kg] | WSD [mm] |
| --- | --- | --- | --- |
| none | — | 130 | 0.82 |
| 1 | 1.0 | 160 | 0.50 |
| 2 | 1.0 | 160 | 0.56 |
| 3 | 1.0 | 160 | 0.56 |
| 4 | 1.0 | 160 | 0.55 |

Example 6: Test for stabilisation against oxidative degradation (TFOUT: Thin Film Oxygen Uptake Test)

This test is a modified version of the Rotary Bomb Oxidation Test for Mineral Oils (ASTM D 2272) and is recognised by the National Bureau of Standards (NBS), Washington D.C. A full description will be found in "C. S. Ku, S M. Hsu, Lubrication Engineering 40, 75–83 (1984)". The test oil is commercially available 15 W 40 motor oil that contains about half the usual amount of zinc dialkyldithiophosphate (0.75% ZnDTP, 550 ppm P, 1160 ppm Zn).

The test additive is dissolved in the test oil to a concentration of 0.5% by weight and heated to 160° C. in an oil bath under an oxygen pressure of 610 kPa in the presence of 2% of water, 4% of an oxidised and nitrated fraction of a motor fuel and 4% of a liquid metal naphthenate as catalysts (supplied under the No. Standard Reference Material 1817 by the NBS). Rotation at 100 rpm at an axial angle of 30° causes an oil film to form on the inner wall of the glass container. After a so-called induction time the oil begins to oxidise, as observed in the rapid fall in oxygen pressure. The test oil itself is subjected to the same procedure. The induction time is recorded as test result. The longer this time is, the more stable the oil mixture is to oxidation.

The results are summarised in Table II.

TABLE II

| Compound of Example | Amount added [%] | Induction period [min] |
| --- | --- | --- |
| none | — | 83 |
| 1 | 0.5 | 117 |
| 2 | 0.5 | 152 |
| 3 | 0.5 | 151 |
| 4 | 0.5 | 133 |

What is claimed is:

1. A compound of formula I

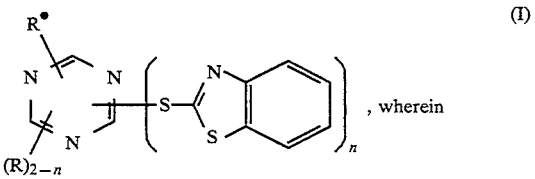, wherein wherein
   n is 1 or 2,
   R and R• are each independently of the other $-OR_1$, $-SR_2$ or $-NR_3R_4$,
   $R_1$ is $C_1-C_{30}$alkyl, $C_5-C_7$cycloalkyl, phenyl or naphthyl, phenyl- or naphthyl-substituted $C_1-C_{18}$alkyl or phenyl or naphthyl which are substituted by $C_1-C_{12}$alkyl, $C_1-C_{12}$alkoxy or $C_1-C_{12}$hydroxyalkyl,
   $R_2$ is $C_1-C_{30}$alkyl, phenyl or naphthyl, phenyl- or naphthyl-substituted $C_1-C_{18}$alkyl or phenyl or naphthyl which are substituted by $C_1-C_{12}$alkyl, $C_1-C_{12}$alkoxy or $C_1-C_{12}$hydroxyalkyl, or is a radical of formula $(CH_2)_p-CO-OR_5$,
   p is 1 or 2,
   $R_3$ and $R_4$ have each independently of the other the meanings of $R_1$, or $-NR_3R_4$ is piperidyl, pyrrolidyl or azepyl, and
   $R_5$ is hydrogen, $C_1-C_{30}$alkyl, $C_5-C_7$cycloalkyl, phenyl or naphthyl, phenyl- or naphthyl-substituted $C_1-C_{18}$alkyl or phenyl or naphthyl which are substituted by $C_1-C_{12}$alkyl, $C_1-C_{12}$alkoxy or $C_1-C_{12}$hydroxyalkyl.

2. A compound according to claim 1, wherein $R_1$ is $C_1-C_{18}$alkyl, $R_2$ is $C_1-C_{18}$alkyl or $CH_2-CO-OR_5$, $R_3$ and $R_4$ are each independently of the other hydrogen, $C_1-C_{18}$alkyl or benzyl, or $-NR_3R_4$ is piperidyl, pyrrolidyl or azepyl, and $R_5$ is $C_1-C_{18}$alkyl.

3. A compound according to claim 1, wherein R and R• are each independently of the other $-SR_2$ or $-NR_3R_4$, $R_2$ is $C_4-C_{12}$alkyl, $R_3$ and $R_4$ are each independently of the other $C_1-C_{12}$alkyl, and $R_5$ is $C_1-C_{18}$alkyl.

4. A compound according to claim 1, wherein n=2, $R_2$ is octyl or $CH_2-CO-O-R_5$, and $R_1$, $R_3$, $R_4$ and $R_5$ are n-octyl, 2-ethylhexyl or isooctyl.

5. A compound according to claim 1, wherein n=1, R and R• are $-SR_2$ and $R_2$ is $CH_2-CO-O-$isooctyl or $CH_2-CO-OR_5$.

6. A composition comprising
   A) lubricant, a hydraulic fluid or a machining fluid, and
   B) at least one compound of formula I

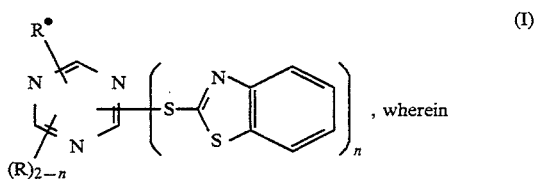, wherein wherein
   n is 1 or 2,
   R and R• are each independently of the other $-OR_1$, $-SR_2$ or $-NR_3R_4$,
   $R_1$ is hydrogen, $C_1-C_{30}$alkyl, $C_5-C_7$cycloalkyl, phenyl or naphthyl, phenyl- or naphthyl-substituted $C_1-C_{18}$alkyl or phenyl or naphthyl which are substituted by $C_1$-$C_{12}$alkyl, $C_1$-$C_{12}$alkoxy or $C_1$-$C_{12}$hydroxyalkyl, $R_2$ is $C_1$-$C_{30}$alkyl, phenyl or naphthyl, phenyl- or naphthyl-substituted $C_1$-$C_{18}$alkyl or phenyl or naphthyl which are substituted by $C_1$-$C_{12}$alkyl, $C_1$-$C_{12}$alkoxy or $C_1$-$C_{12}$hydroxyalkyl, or is a radical of formula $(CH_2)_p$—CO—OR$_5$, p is 1 or 2, $R_3$ and $R_4$ have each independently of the other the meanings of $R_1$, or —NR$_3$R$_4$ is piperidyl, pyrrolidyl or azepyl, and $R_5$ is hydrogen, $C_1$-$C_{30}$alkyl, $C_5$-$C_7$cycloalkyl, phenyl or naphthyl, phenyl- or naphthyl-substituted $C_1$-$C_{18}$alkyl or phenyl or naphthyl which are substituted by $C_1$-$C_{12}$alkyl, $C_1$-$C_{12}$alkoxy or $C_1$-$C_{12}$hydroxyalkyl.

7. A composition according to claim 6, which additionally comprises one or more than one further additive selected from the group consisting of corrosion inhibitors, rust inhibitors, metal deactivators, viscosity index improvers, dispersants, antioxidants, pour-point depressants, extreme-pressure and antiwear additives.

8. A composition according to claim 6, wherein $R_1$ of formula I is $C_1$-$C_{18}$alkyl, $R_2$ is $C_1$-$C_{18}$alkyl or CH$_2$—CO—OR$_5$, $R_3$ and $R_4$ are each independently of the other hydrogen, $C_1$-$C_{18}$alkyl or benzyl, or —NR$_3$R$_4$ is piperidyl, pyrrolidyl or azapyl, and $R_5$ is $C_1$-$C_{18}$alkyl.

9. A composition according to claim 6, wherein R and R• are each independently of the other —SR$_2$ or —NR$_3$R$_4$, $R_2$ is $C_4$-$C_{12}$alkyl, $R_3$ and $R_4$ are each independently of the other $C_1$-$C_{12}$alkyl, and $R_5$ is $C_1$-$C_{18}$alkyl.

10. A composition according to claim 6, wherein n=2, $R_2$ is octyl or CH$_2$—CO—R$_5$, and $R_1$, $R_3$, $R_4$ and $R_5$ are n-octyl, 2-ethylhexyl or isooctyl.

11. A composition according to claim 6, wherein n=1, R and R• are —SR$_2$ and $R_2$ is CH$_2$—CO—O—i-sooctyl or CH$_2$—CO—OR$_5$.

12. A process for enhancing the performance properties of lubricant compositions, hydraulic fluids and machining fluids, which comprises adding thereto at least one compound of formula I

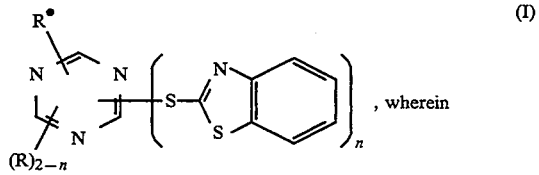
, wherein wherein n is 1 or 2,

R and R• are each independently of the other —OR$_1$, —SR$_2$ or —NR$_3$R$_4$, $R_1$ is hydrogen, $C_1$-$C_{30}$alkyl, $C_5$-$C_7$cycloalkyl, phenyl or naphthyl, phenyl- or naphthyl-substituted $C_1$-$C_{18}$alkyl or phenyl or naphthyl which are substituted by $C_1$-$C_{12}$alkyl, $C_1$-$C_{12}$alkoxy or $C_1$-$C_{12}$hydroxyalkyl, $R_2$ is $C_1$-$C_{30}$alkyl, phenyl or naphthyl, phenyl- or naphthyl-substituted $C_1$-$C_{18}$alkyl or phenyl or naphthyl which are substituted by $C_1$-$C_{12}$alkyl, $C_1$-$C_{12}$alkoxy or $C_1$-$C_{12}$hydroxyalkyl, or is a radical of formula $(CH_2)_p$—CO—OR$_5$, p is 1 or 2, $R_3$ and $R_4$ have each independently of the other the meanings of $R_1$, or —NR$_3$R$_4$ is piperidyl, pyrrolidyl or azepyl, and $R_5$ is hydrogen, $C_1$-$C_{30}$alkyl, $C_5$-$C_7$cycloalkyl, phenyl or naphthyl, phenyl- or naphthyl-substituted $C_1$-$C_{18}$alkyl or phenyl or naphthyl which are substituted by $C_1$-$C_{12}$alkyl, $C_1$-$C_{12}$alkoxy or $C_1$-$C_{12}$hydroxyalkyl.

* * * * *